United States Patent [19]
Kauffman et al.

[11] Patent Number: 5,480,808
[45] Date of Patent: Jan. 2, 1996

[54] VOLTAMMETRIC METHOD FOR MEASURING PEROXIDE CONCENTRATION IN HYDROCARBON FUELS

[75] Inventors: Robert E. Kauffman, Centerville; James D. Wolf, Kettering, both of Ohio

[73] Assignee: The Unversity of Dayton, Dayton, Ohio

[21] Appl. No.: 378,480

[22] Filed: Jan. 26, 1995

Related U.S. Application Data

[63] Continuation-in-part of Ser. No. 189,516, Jan. 31, 1994, abandoned.

[51] Int. Cl.$^6$ .......................... G01N 33/26; G01N 33/03
[52] U.S. Cl. ..................... 436/135; 422/82.02; 436/20; 436/149; 436/150; 436/151
[58] Field of Search .............................. 422/82.01, 82.02; 436/20, 125, 135, 149, 150, 127, 129, 151

[56] References Cited

U.S. PATENT DOCUMENTS

| | | | |
|---|---|---|---|
| 4,029,554 | 6/1977 | Ellison | 204/1 T |
| 4,744,870 | 5/1988 | Kauffman | 436/60 X |
| 4,764,258 | 8/1988 | Kauffman | 436/60 X |
| 5,071,527 | 12/1991 | Kauffman | 204/153.1 |
| 5,098,547 | 3/1992 | Bryan et al. | 204/401 |
| 5,200,027 | 4/1993 | Lee et al. | 156/651 |
| 5,239,258 | 8/1993 | Kauffman | 204/153.1 X |

FOREIGN PATENT DOCUMENTS

| | | |
|---|---|---|
| 326421 | 8/1989 | European Pat. Off. . |

OTHER PUBLICATIONS

O. D. Shapilov *J. Anal. Chem. USSR* 1968, 23, 1629–1630.
U. Fiedler *Talanta* 1973, 20, 1097–1104.
U. Fiedler *Talanta* 1973, 20, 1309–1317.
U. Fiedler *J. Am. Oil Chem. Soc.* 1974, 51, 101–103.
L. R. Sharma et al. *Analyst* 1976, 101, 55–61.
N. Yanishlieva et al. *Chem. Abstr.* 1984, 101, 20084n.
J. A. Plambeck "Electroanalytical Chemistry Basic Principles and Applications" John Wiley & Sons: New York, 1982, pp. 307–320.
M. A. Voronina et al. *Chem. Abstr.* 1985, 102, 48407q.
J. Polak et al. *Analyst* 1986, 111, 1207–1210.
S. Uchiyama et al. *Chem. Abstr.* 1990, 113, 189859c.
M. Oishi et al. Chem. Abstr. 1992 117, 46858y.

*Primary Examiner*—James C. Housel
*Assistant Examiner*—Arlen Soderquist
*Attorney, Agent, or Firm*—Killworth, Gottman, Hagan & Schaeff

[57] ABSTRACT

A method for the analysis of peroxide in hydrocarbon fuels such as jet fuels, diesel fuel, kerosene and gasoline is disclosed which can be performed both at remote locations as well as in a laboratory setting. A sample of the fuel to be tested is mixed with a solution containing a water-soluble salt and aqueous iodide solution to reduce the peroxide and produce free iodine. The sample is then subjected to a single sweep voltammetric analysis to measure the current through the sample as a function of the potential applied. The resulting peak of current on a current-potential plot can then be used to determine the amount of peroxide in solution.

12 Claims, 2 Drawing Sheets

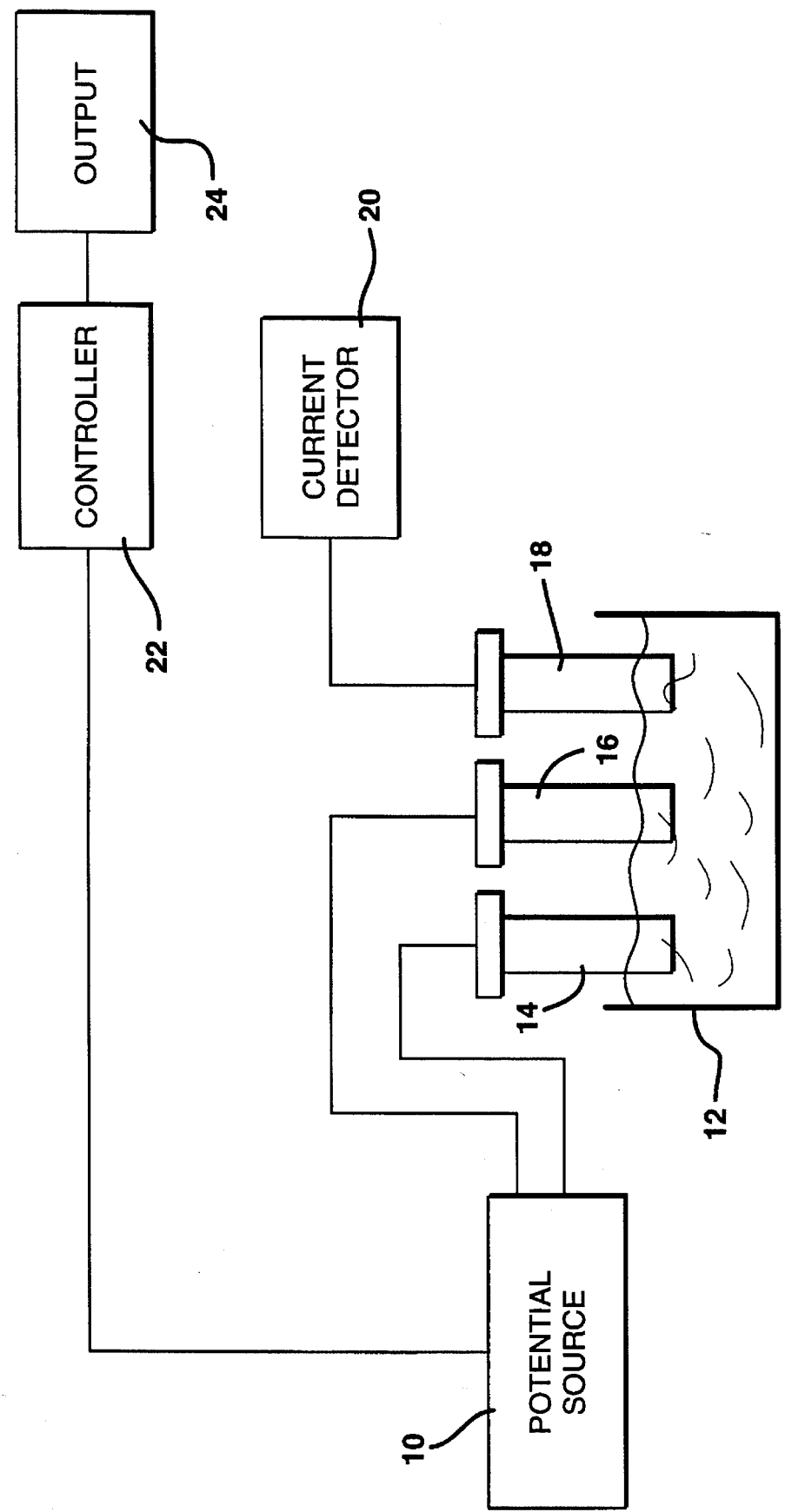

VOLTAMMETRIC METHOD FOR MEASURING PEROXIDE CONCENTRATION IN HYDROCARBON FUELS

The United States government has rights in this invention, pursuant to Contract No. F33615-92-C-2207 awarded by the Department of the Air Force.

This application is a continuation-in-part of prior U.S. patent application 08/189,516 filed Jan. 31, 1994, now abandoned.

BACKGROUND OF THE INVENTION

The present invention relates generally to determining the peroxide content of materials which may contain peroxide, more specifically, to a method and apparatus for determining the peroxide content of hydrocarbon fuels, such as, jet fuels and diesel fuels.

Hydrocarbon fuels, such as jet fuel, gasoline, diesel fuel and kerosene, are typically stored for a period of time before use. During transportation, bulk storage or storage in engine tanks or other containers, hydrocarbon fuels are frequently subject to the oxidative formation of peroxide compounds in the fuel, in particular, the formation of hydroperoxides. The presence of these peroxides accelerates both the formation of gums, sediments, and other insoluble substances in the stored fuels and the degradation of engine components. Thus, stored and transported hydrocarbon fuels need to be monitored for peroxide formation.

Peroxide in fuels degrades to aldehydes. The thermal input typically experienced by fuels further causes aldehydes to produce carboxylic acids and phenols. The use of a fuel can result in excessive component wear and eventual equipment failure. It is undesirable to use fuels beyond their useful life. However, as a conservative precautionary measure, fuels left in storage may require premature re-refining, reprocessing or disposal. This approach, consequently, results in the premature discard of fuel with useful lives. Early detection of content is important in monitoring the continued viability of fuel. Early detection would allow more efficient use of these materials thereby saving in material, labor and equipment costs.

Peroxide content can be measured with commercially available peroxide teststrips, such as for example, MERCKOQUANT 10011 PEROXIDE TEST, from EM Science of Gibbstown, N.J. However, peroxide test strips are not acceptable to hydrocarbon fuel users since the test strips produce an approximate range of peroxide content, are based on hydrogen peroxide not organic hydroperoxides present in stored fuels, and require a volatile, peroxide-free ether for dilution purposes prior to testing.

The only test formerly acceptable for performing peroxide evaluations of jet fuels is ASTM Method D3703-85 titled "Standard Test Method for Peroxide Number of Aviation Turbine Fuels". The ASTM method is a titration method in which a quantity of fuel is dissolved in an chlorinated solvent and mixed with potassium iodide. The potassium iodide reduces the peroxides present in the fuel. An equivalent amount of iodine is then liberated. The peroxide level in the fuel is then determined by titration of the liberated iodine with sodium thiosulfate solution.

The ASTM method has a number of distinct drawbacks which make routine and remote peroxide measurement impractical. It is time consuming, tedious and expensive. First, as the ASTM method requires a titration, remote on site analysis is very impractical due to the fragility of the equipment, chemicals required and expertise of personnel required to conduct the titration. Further, the ASTM method generates up to 460 milliliters of chlorinated waste per sample tested. Due to environmental considerations, the use of chlorinated solvents is quite costly due to special waste disposal methods required for chlorinated waste. Multiple testing of a sample is impossible as each titration requires a fresh solution. Finally, 11 minutes of time are required per sample analyzed. Thus, for triplicate analysis of a supply of fuel over 30 minutes in a laboratory would be required.

U.S. Pat. Nos. 4,744,870 and 5,071,527 to co-inventor Kauffman disclose the voltammetric analysis of antioxidant containing oils and lubricants. A sample is mixed with a solvent, an electrolyte and an organic base. A potential is then swept across the sample while measuring the current. However, neither the '870 patent or the '527 patent measure peroxide level nor do they add an aqueous solution of potassium iodide. Rather, they both measure the amount of remaining antioxidant in the oil or lubricant to determine the remaining useful life of the oil or lubricant.

U.S. Pat. Nos. 4,764,258 and 5,239,258 also to Kauffman relate to voltammetric methods for evaluating lubricating oils in the former and fuels, food and oils in the latter. A sample is mixed with a solvent, an electrolyte and then subject to sweeping potential while the current is measured. However, in U.S. Pat. No. 4,764,258, an antioxidant additive is analyzed for while in the U.S. Pat. No. 5,239,258 the degradation products analyzed are aldehydes and phenols. Peroxides are not analyzed in either patent. Both patents also do not add an aqueous solution of iodide and, thus, cannot determine peroxide levels in a sample.

Accordingly, there remains a need for quick, accurate determination of peroxides in hydrocarbon fuels which may contain peroxide including jet fuel, diesel fuel and gasoline.

SUMMARY OF THE INVENTION

The present invention solves this need by providing a method for measuring the peroxide concentration of hydrocarbon fuels such as jet fuel and diesel fuel. The method can be used to measure peroxide concentration at remote locations such as storage or transportation facilities. Further, the method can be used to measure the peroxide concentration in a laboratory setting.

In accordance with the present invention a voltammetric method for measuring the peroxide level in hydrocarbon fuels containing peroxide is provided. The method is accomplished by mixing a sample or supply of the fuel to be tested with an aqueous acidic solution of an iodide compound, preferably potassium iodide and a solution of a water-soluble salt. The iodide compound reacts with any peroxide existing in the supply of fuel to reduce the peroxide. The reaction generates an amount of iodine equivalent to the amount of peroxide present.

The reacted supply of fuel is placed into contact with electrodes of a device for performing voltmmetry. The electrodes can include a working electrode, a reference electrode and an auxiliary electrode. Further, all the electrodes can be encased in a single probe for ease of use.

An electric potential is then applied across the electrodes in the reacted supply of fuel to create a current through the reacted solution. The potential is applied as a voltage which is linear with time. That is, the potential is started at a first potential value and gradually either increased or decreased to a second potential value. In the present invention, the potential is swept in the range of from 1.0 V to about −1.5 V. Preferably, the first potential value is 0 V and the second potential value is −1.0 V. As the potential is being swept, the current of the solution is measured as a function of the potential and recorded.

From, the values of current as a function of potential, it is possible to calculate the peroxide concentration of the supply of fuel. The above voltammetric analysis is performed on a blank iodine solution and on a standard iodine solution. These values are then compared to the values obtained for the reacted supply of material.

It is within the scope of this invention that the steps of applying the potential, varying the potential and measuring the current as a function of the potential are all performed by a single voltammetric device. It is also within the scope that the voltammetric device is operated by a device which further compares the current values for all solutions and calculates the peroxide levels in the supply of fuel.

The supply of fuel to be measured by the present invention can be any fuel which may contain peroxide. In particular, the supply of material can be a jet fuel, gasoline, diesel fuel, or kerosene. The peroxide measured in the present invention can be any of the known peroxides including, for example, single peroxide compounds, diperoxide compounds, and hydroperoxides. In particular, the method comprises measuring hydroperoxides as they are the most frequently found peroxide in hydrocarbon fuels. Additionally, if it is desired to analyze diperoxide compounds, alcoholic sodium iodide may be used as the iodide containing solution inconjunction with a heating step in order to reduce the diperoxide.

Accordingly, it an object of the present invention to provide a method and apparatus for measuring the peroxide level in a supply of fuel which is fast, accurate and easily measures peroxide. It is another object of the invention to provide a method to measure the peroxide level of a supply of fuel which is both capable of use at a remote location as well as in a laboratory. It is still another object of the present invention to provide a method for measuring peroxide levels that can be either automated or manually operated. Other objects and advantages of the present invention will be apparent from the following description, the accompanying figures, and the claims.

BRIEF DESCRIPTION OF THE DRAWINGS

FIG. 3 is a block diagram of the system of the present invention.

DETAILED DESCRIPTION OF THE PREFERRED EMBODIMENT

Figure 1:
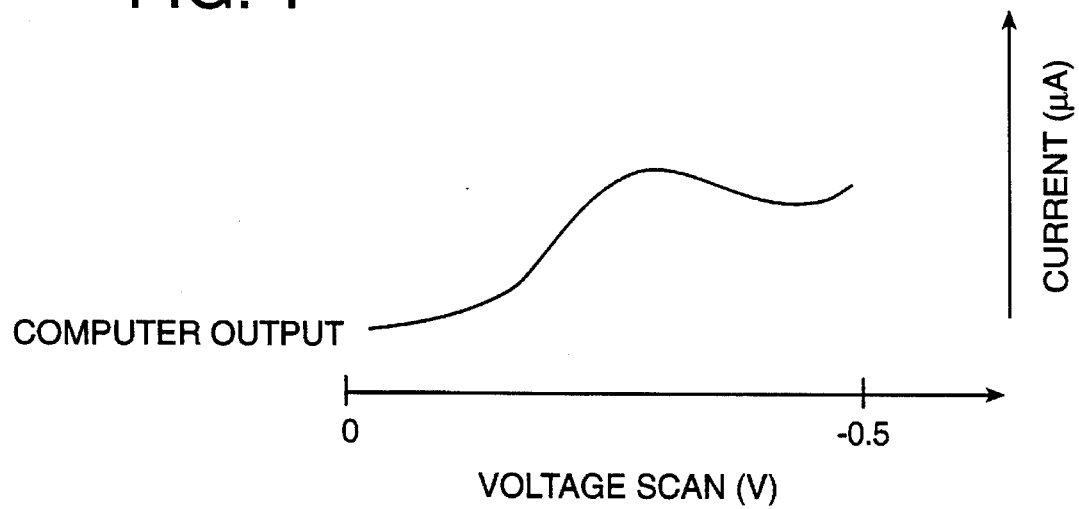
FIG. 1 is a current versus potential plot as used in the first formula for calculating peroxide content.

The method for measuring the peroxide level of fuel containing peroxide, in accordance with the present invention, is based upon voltammetric analysis of a sample of the material. In general, voltammetric techniques are electroanalytical methods wherein electrodes are placed in a sample to be tested. Data is obtained by measuring the current passing through the sample as a function of the potential applied, and test results are based on current, voltage, and time relationships at the electrodes.

In performing a voltammetric analysis, the potential across the electrodes is varied linearly with time, and the resulting current is recorded as a function of the potential. In accordance, with the present invention, an initial potential applied to the electrodes of first value E1 is linearly increased over time to a second value E2. The voltage scan rate can be any rate, but is preferably 0.1 V/sec. The potential is swept in the range of from 1.0 V to about −1.5 Vo Preferably, the first potential value is 0 V and the second potential value is −1.0 V.

While cyclic voltammetry can be employed (i.e. varying potential over time through a complete cycle), the present invention preferably employs a single sweep of potential. A cyclic sweep of potential may oxidize unreacted iodide compound and generate an inflated reading. The voltammetric analysis of the present invention is similar to that employed in earlier works of an inventor herein, namely U.S. Pat. Nos. 4,744,870, 4,764,258, 5,071,527, and 5,239,258, of which, the disclosures of each are herein incorporated by reference.

In practicing the method of the present invention it is possible to easily determine the peroxide level of a sample. The peroxides capable of being measured include all peroxide compounds such as, for example, single peroxide compounds, diperoxide compounds and hydroperoxide compounds. This determination is achieved by first reducing the peroxide with an acidic iodide containing solution. The iodide reduces the peroxide and forms an amount of iodine corresponding to the peroxide amount in the material tested. Any known iodide solution can used in practicing the present invention, however, potassium iodide is preferred. Further, if one desires to measure the level of diperoxide compounds, an alcoholic iodide solution such as alcoholic sodium iodide may be employed in conjunction with a heating step in order to reduce the diperoxide.

The fuel sample to be tested may also be mixed with a solution containing a water-soluble salt. The water-soluble salt acts to increase the solubility of certain polar species in the fuel layer, such as, for example phenol, which are present in various fuels, such as diesel fuel, and prevent the complete separation of the aqueous and fuel layers. Addition of a water-soluble salt decreases the time required for the separation of the fuel and aqueous layers by increasing solubility in the fuel layer while decreasing solubility in the aqueous layer. Fuels which have relatively few of these polar species, such as jet fuels or gasoline, may not require the addition of a water-soluble salt. However, fuels which contain a higher level of impurities, such as diesel fuel, will require the addition of a water-soluble salt. Any water-soluble salt may be employed in the present invention. However, the water-soluble salt is preferably a potassium chloride solution.

Once the sample has been reacted with iodide to reduce peroxide and form free iodine, and, if desired, the solution of a water-soluble salt, the solution is subjected to a voltammetric analysis as described above. The reacted sample solution is brought into contact with the electrodes of a voltammetric device. A potential is applied to the solution to generate a current therethrough. The potential is varied in a sweep from a first potential value to a second potential value on either side of the reduction potential of iodine. And, the current generated as free iodine is reduced is measured and recorded as a function of potential.

The system is preferably, but not exclusively, controlled by a internal microprocessor in the voltammetric device. With internal microprocessor control, the peroxide level can be calculated by the voltammetric device itself. The current measured as a function of potential will result in a maximum value at the reduction potential of iodine. From this peak, the peroxide level may be calculated by either of two different methods.

In the first method for calculating peroxide levels, the peak of the current versus potential curve such as is shown in FIG. 1 is measured and a value for peak height is obtained corresponding to the maximum amount of current generated. This peak height value can be compared to similar values obtained for blank and standard iodine solutions. Peroxide content can be calculated from the following equation:

$$\text{Peroxide (mM)} = \frac{(\text{Peak height for Sample} - \text{Peak height for Blank})}{(\text{Peak height for Standard} - \text{Peak height for Blank}) \times \text{Sample Size (mL)}} \quad (1)$$

where mM is millimoles and mL is milliliters. The entire calculation can be performed by the internal microprocessor to aid in the ease of operation of the system.

Figure 2:
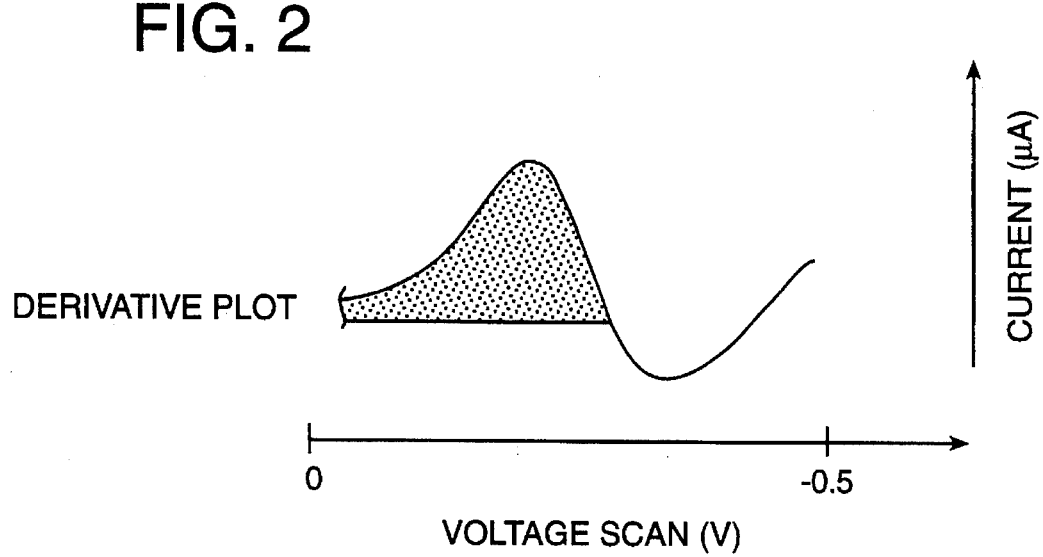
FIG. 2 is a current versus potential plot as used in the second formula for calculating peroxide content.

In the second method, current is recorded in a plot versus potential curve, again generating a peak corresponding to iodine. Through means of a microprocessor, the area under the peak, as can be seen in FIG. 2, can be calculated to produce a peak area for iodine. Peak area is also calculated for blank and standard iodine solutions. Peroxide content can then be calculated from the following equation:

$$\text{Peroxide (mM)} = \frac{(\text{Peak Area for Sample} - \text{Peak Area for Blank})}{(\text{Peak Area for Standard} - \text{Peak Area for Blank}) \times \text{Sample Size (mL)}} \quad (2)$$

where mM is millimoles and mL is milliliters. Preferably, the current is displayed as a derivative plot of current versus potential. The peak area of the positive derivative corresponding to iodine is then used. The use of derivative plots allows a more thorough analysis of weaker signals from smaller samples.

The electrodes of the present invention may consist of any number of electrodes including a working electrode, a reference electrode and an auxiliary electrode. The working electrode, reference electrode, and auxiliary electrode may be made from any conductive material. However, glassy carbon is preferred for the working electrode, and platinum is preferred for the auxiliary and reference electrodes. The potential is applied to the auxiliary electrode while the current generated is measured at the working electrode. The reference electrode functions to help keep the potential on the auxiliary electrode at the proper level. The electrodes may be enclosed in a single probe. A single probe is significantly easier to operate and requires a smaller sample size to be tested.

The voltammetric device and system may be employed as a single hand-held device or connected to an external microprocessor. When employed as a single hand-held device, the first method for calculating peroxide is preferably employed. When connected to an external microprocessor, the second method for calculating peroxide is preferably employed. The second method is capable of greater data analysis and manipulation which is easily performed with an external microprocessor.

As mentioned previously, the present invention is equally functional as a remote testing method, i.e. at the storage or transportation site, or as a laboratory test method. For remote location analysis, the single hand-held device can be employed. The hand-held device has a single probe as mentioned previously. A standard solution containing peroxide may be employed. The standard contains an amount of peroxide equal to the allowed peroxide level of the fuel, for example about 0.4 mM of peroxide. The test sample is prepared by adding acidic iodide containing solution and the water-soluble salt, if desired, shaking and then diluting with water. The aqueous layer of the test sample, a blank and a standard are subjected to voltammetric analysis as described above and a signal reading for each is obtained.

The signal represents the peak height of the iodine reduction. If the signal reading for the sample is below the signal reading for the standard, the sample has lower peroxide levels than the standard and thus, is below the allowed peroxide level for the fuel. If the reading of the sample exceeds the standard reading, the peroxide level can be calculated from formula (1) by means of the internal microprocessor. The operator can then use established guidelines to decide the unsuitability of the sample and monitor the peroxide accumulation rate.

If a laboratory analysis is desired, the analysis is conducted as above. However, the system is preferably connected to an external microprocessor such as a computer. Method two is then used to calculate peroxide levels.

A block diagram of the system of the present invention is represented in FIG. 3. With reference to FIG. 3, there is seen a source of varying potential 10. The potential source is connected with auxiliary electrode 14 and reference electrode 16. A working electrode 18 is then connected to a means for measuring the current generated 20. All three electrodes 14, 16, and 18 are placed in contact with a sample containing iodine and placed in a vessel 12 for holding the sample. The current measuring device 20 is connected to a controller 22 such as dedicated circuitry or a microprocessor. The controller 22 is connected both to the potential source and a means for output of the current measured.

The method of the present invention may be used to measure peroxide levels in any fuel which may contain peroxide. Such fuels include, but are not limited to, jet fuel, diesel fuel, gasoline or kerosene. However, additional fuels may be included in the present invention.

The method of the present invention is a significant improvement over the prior art. As mentioned previously, the only previously approved method for testing fuels for peroxides was the ASTM D3703-85 method. The present invention is clearly a superior testing method to the ASTM method. The present method is 15 times faster than the ASTM method, requires 10 times less fuel as a sample, produces 60 times less waste, does not require chlorinated solvents, and does not require continuous purging with nitrogen. Further, the method does not require special operator skill to perform while titration does. Table 1 shows a comparison of the method of the present invention and more clearly points out the superior benefits of the present invention.

TABLE 1

Comparison of Experimental Features Used by ASTM Method and the Method of the Present Invention

| Experimental Features | ASTM | Present Invention |
| --- | --- | --- |
| Fuel Sample Size | up to 60 ml | up to 5 ml |
| Reaction Vessel | 250 ml Flask | 10 ml vial |
| Halogenated Solvent | 25 ml | No |
| (Nitrogen Flush - 1 minute) | | |
| Continuous Nitrogen Flush | Yes | No |
| Acetic Acid Solution | 20 ml | 1 ml |
| Potassium Iodide Solution | 2 ml | 0.2 ml |
| Agitation and Setting Time | 6 minutes | 30 seconds |
| Water Dilution | 100 ml | 1 ml |
| Iodine Detection | Titration - Starch indicator | Voltammetric - Peak Height or Area |

TABLE 1-continued

Comparison of Experimental Features Used by ASTM Method and the Method of the Present Invention

| Experimental Features | ASTM | Present Invention |
| --- | --- | --- |
| Iodine Detection Time | 5 minutes | 5 seconds |
| Iodine Detection Duplication | No, New sample required | Yes |
| Total Waste per Analysis | up to 460 ml | up to 7 ml |
| Total Analysis Time | | |
| Single Analyses | 11 minutes | 40 seconds |
| Duplicate Analyses | 22 minutes | 50 seconds |
| Triplicate Analyses | 33 minutes | 1 minute |

The method of the present invention will now be illustrated by reference to several examples. The method is not intended to be limited to the specific, exemplary materials but, rather, may be practiced generally by the principles espoused below.

Comparison Example

ASTM Method D3703-85 was performed as specified in the method except that the fuel quantity was measured by volume instead of weight and concentration of hydroperoxide was calculated in millimole per liter (mM) instead of in part per million. The one part per million of hydroperoxide determined by the ASTM method is equal to 0.05 mM of hydroperoxide.

For this study test fuels were prepared containing known quantities of various peroxides and hydroperoxides as listed in Table 2. The fuel employed was unstressed jet fuel (Jet A-1). 1–5 ml of each fuel was dispensed into a 250 mL erlenmeyer flask that was flushed continuously with nitrogen. Into the flask were added in succession without interruption of the nitrogen flow: 25 mL of 1,1,2 trichloro-1,2,2 trifluoroethane, 20 mL of acetic acid solution/hydrochloric acid solution (100:1), and 2mL of saturated potassium iodide solution. The flask was swirled for thirty seconds and set aside for 5 minutes. 10.0 mL of water was added to the reaction solution which was then titrated with a sodium thiosulfate solution to a blue endpoint using a starch indicator. The results for each fuel tested are listed in Table 2.

EXAMPLE

The method of the present invention was then performed on the same fuels as employed in the Comparison Example. The same aqueous potassium iodide solutions and acetic/hydrochloric acid solutions as used in the ASTM method are employed here. The voltammetric device was calibrated using a blank (0 mM) and standard (1 mM) iodine solutions.

The blank iodine solution was prepared by dispensing 0.25 mL of potassium iodide, 1 mL of acetic acid solution, and 1 mL of aqueous KCl solution into a 5 mL vial. The 1 mM iodine standard was prepared by dispensing 0.25 mL of potassium iodide, 1 mL of acetic acid solution, and 0.020 mL (using a micropipetter) of 50 mM aqueous potassium dichromate solution into a 5 mL vial. The vial was capped, shaken for approximately 5 seconds, opened, 1 mL of water was added, the vial was recapped and gently shaken for approximately 2 seconds.

The sample solutions were prepared by dispensing 1 to 5 mL of fuel, 0.25 mL of potassium iodide solution, and 1 mL of acetic acid solution into a 10 mL vial. The vial was capped and vigorously shaken by hand for approximately 30 seconds. The vial was opened, 1 mL of aqueous KCl solution added, the vial recapped, and gently shaken for 2 seconds.

The vial was allowed to sit undisturbed for approximately 10 seconds. The vial was reopened and the lower (aqueous) layer of the vial was then pipetted into a new 5 mL vial for analysis.

The blank, standard and fuel sample analyses were performed by inserting the solid probe of the voltammetric device into the 5 mL vial and the potential applied and measured as described above. After, the 5 second analysis period, the area under the resulting iodine peak was integrated and displayed. The peroxide concentration was then calculated from equation 2. The results are listed in Table 2.

TABLE 2

Comparison of the Present Invention with ASTM Method D-3703 Test

| | | Concentration (m Moles/L) | |
| --- | --- | --- | --- |
| Fuel Solutions (1 mL) | Actual (mM) | Present Invention | ASTM (mM) |
| Cumene Hydroperoxide | 1.0 | 1.1 | 0.9 |
| T-Butyl Hydroperoxide | 1.0 | 1.0 | 1.2 |
| Lauroyl Peroxide | 1.0 | 0.1 | 0.0 |
| Dicumyl Peroxide | 1.0 | 0.0 | 0.2 |
| T-Butyl Hydroperoxide | 0.1 | 0.1 | 0.3 |
| T-Butyl Hydroperoxide (5 mL) | 0.02 | 0.03 | 0.4 |

The test results demonstrate that there is good agreement between the ASTM method and the method of the present invention. Further, Table 2 demonstrates that the accuracy of the present method is very good. Thus, the method of the present invention is a significant improvement on the prior art in that it is as accurate, in good agreement as the ASTM method, yet, is 15 times faster, produces 60 times less waste, does not require chlorinated solvent, or continuous nitrogen purging.

While certain representative embodiments and details have been shown for the purposes of illustrating the present invention, it will be apparent to those skilled in the art that various changes in the method disclosed herein may be made without departing from the scope of the invention, which is defined in the appended claims.

What is claimed is:

1. A method for measuring the peroxide content of a fuel comprising:

reacting a supply of fuel to be tested with a solution containing a water-soluble salt and an acidic iodide containing aqueous solution to reduce any peroxide present in said supply of material and produce iodine;

allowing the resulting mixture to separate into an aqueous phase and a fuel phase;

bringing electrodes into contact with the aqueous phase;

applying an electric potential to the aqueous phase to produce an electric current therethrough;

varying the potential in a single sweep from a first potential value to a second potential value; and, measuring and recording the current during said potential sweep;

wherein the peroxide content is determined from the measured current.

2. The method as recited in claim 1 wherein said electrodes include a working electrode, a reference electrode and an auxiliary electrode.

3. The method as recited in claim 2 wherein said reference electrode, said auxiliary electrode and said working electrode are enclosed in a single probe.

4. The method as recited in claim 1 wherein said applying of electric potential step, said varying of potential step and said measuring of current step are all performed by a single voltammetric device.

5. The method as recited in claim 1 wherein said measuring further includes the steps of:
- measuring the current while varying the potential in a blank iodine containing solution;
- measuring the current while varying the potential in a standard iodine containing solution;
- comparing the current measured for said reacted supply of material to the current measured for said blank solution and said standard solution; and,
- calculating said peroxide concentration in said supply of fuel.

6. The method as recited in claim 1 wherein said first and second potential values are in the range of from 1.0 V to about −1.5 V.

7. The method as recited in claim 6 wherein said first potential value is 0 V and said second potential value is −1.0 V.

8. The method as recited in claim 1 wherein said supply of fuel is selected from the group consisting of jet fuel, diesel fuel, gasoline, or kerosene.

9. The method as recited in claim 1 wherein said water-soluble salt is potassium chloride.

10. The method as recited in claim 1 wherein said acidic iodide containing solution is aqueous potassium iodide or alcoholic sodium iodide.

11. The method as recited in claim 1 wherein the peroxide measured is selected form the group consisting of single peroxides, diperoxides, or hydroperoxides.

12. The method as recited in claim 1 wherein said acidic iodide containing solution is aqueous potassium iodide and said peroxide measured is hydroperoxide.

* * * * *